United States Patent [19]

Burk et al.

[11] 4,190,668

[45] Feb. 26, 1980

[54] STABILIZED AQUEOUS AMIDE ANTIMICROBIAL COMPOSITION

[75] Inventors: George A. Burk, Bay City; Charles A. Wilson, Midland, both of Mich.

[73] Assignee: The Dow Chemical Company, Midland, Mich.

[21] Appl. No.: 860,497

[22] Filed: Dec. 14, 1977

[51] Int. Cl.$^2$ .............................................. A01N 9/20
[52] U.S. Cl. ................... 424/304; 424/248.4; 424/278; 424/285; 424/320
[58] Field of Search ............... 424/304, 320, 285, 278, 424/248.4

[56] References Cited

U.S. PATENT DOCUMENTS

| | | | |
|---|---|---|---|
| 3,689,660 | 9/1972 | Burk et al. | 424/304 |
| 3,751,444 | 8/1973 | Solem et al. | 260/465.4 |
| 4,022,605 | 5/1977 | Konya et al. | 424/304 |

Primary Examiner—V. D. Turner
Attorney, Agent, or Firm—James B. Guffey

[57] ABSTRACT

Aqueous antimicrobial compositions which comprise a halogenated amide antimicrobial, such as 2,2-dibromonitrilopropionamide, a water miscible organic solvent such as a straight chain polyalkylene glycol (e.g., polyethylene glycol 200) or an ether thereof (e.g., a mono- or di- lower alkyl and/or phenyl ether) and water are stabilized against decomposition of the halogenated amide antimicrobial by the addition of a cyclic ether stabilizer such as tetrahydrofuran, tetrahydropyran, 1,4-dioxane, sym-trioxane, N-methyl morpholine, etc. The compositions, so stabilized, exhibit reduced rates of decomposition of the halogenated amide antimicrobial relative to the corresponding non-stabilized aqueous compositions.

19 Claims, No Drawings

STABILIZED AQUEOUS AMIDE ANTIMICROBIAL COMPOSITION

BACKGROUND OF THE INVENTION

This invention relates to stabilized aqueous antimicrobial compositions which comprise a halogenated amide as the active (i.e., antimicrobial) ingredient and to processes for their preparation.

Halogenated amides such as 2,2-dibromonitrilopropionamide are useful as antimicrobials in various applications. See, for example, Nolan et al., U.S. Pat. No. 2,419,888; Schmidt et al., U.S. Pat. No. 3,493,658; and CIBA S.A. Belgian Patent No. 668,336. Certain halogenated amides are useful in the finishing of textiles, as taught by Chance et al., U.S. Pat. Nos. 3,350,164 and 3,403,174. Others are useful as slimicides in aqueous systems such as paper pulp and cooling towers and as sterilizing agents for drycleaning fluids. See, for example, Wolf, U.S. Pat. No. 3,647,610; Wolf, U.S. Pat. No. 3,649,166; Wolf et al., "2,2-Dibromo-3-Nitrilopropionamide, A Compound with Slimicidal Activity", *Applied Microbiology*, Vol. 24, No. 4, pp. 581–584 (1972); and Moyle et al., U.S. Pat. No. 3,928,575.

In the storage, shipment and use of such antimicrobial agents, it is often desirable to employ the antimicrobial agent in the form of a liquid concentrate composition wherein the halogenated amide antimicrobial is dissolved in a mixture of an organic solvent and water. However, the presence of water in such compositions often accelerate decomposition of the halogenated amide antimicrobial. See, for example, U.S. Pat. No. 3,689,660 and "Rates and Products of Decomposition of 2,2-Dibromo-3-Nitrilopropionamide", Exner et al., *J. Agr. Food Chem.*, Vol. 21, No. 5, pp. 838–842 (1973). Accordingly, in order to obtain adequate stability for many purposes, it has heretofore been necessary to resort to essentially anhydrous liquid concentrate compositions and it has therefore been necessary to essentially exclude water from the ingredients used in the preparation thereof.

Consequently, it is desirable to provide a means of reducing the adverse impact of water upon the aforementioned liquid concentrate compositions and to thereby provide (a) aqueous halogenated amide antimicrobial compositions having improved stability and (b) simplified, economical processes for the preparation of stable liquid concentrate compositions.

SUMMARY OF THE INVENTION

It has now been found that the rate of decomposition of the halogenated amide antimicrobial in the aforementioned aqueous liquid concentrate compositions is substantially reduced by the addition of a 5- or 6-membered saturated cyclic ester stabilizer or an inertly substituted 5- or 6-membered saturated cyclic ether stabilizer. Thus, in one aspect the instant invention is a stabilized aqueous antimicrobial composition, which comprises (1) a water miscible organic solvent; (2) water; (3) a halogenated amide antimicrobial; and (4) a stabilizing amount of a 5- or 6-membered saturated cyclic ether stabilizer or an inertly substituted 5- or 6-membered saturated cyclic ether stabilizer. Typically, such composition has a pH of from about 2 to about 5 (preferably from about 3 to about 4).

In another aspect the instant invention is a process for preparing an aqueous halogenated amide antimicrobial composition wherein the aqueous component of such composition comprises the aqueous reaction medium in which the halogenated amide antimicrobial was prepared. Such process comprises the steps of:

(a) preparing the halogenated amide antimicrobial by the acid catalyzed reaction of a non-halogenated amide with halogen in aqueous solution;

(b) dissolving the resulting aqueous reaction mixture in a water miscible organic solvent; and (c) adding to the reaction mixture, or to the water miscible organic solvent solution thereof, a stabilizing amount of a 5- or 6-membered saturated cyclic ether or an inertly substituted 5- or 6-membered saturated cyclic ether.

Typically, the aforementioned process also involves a pH adjustment step such that the composition resulting from such process has a pH of from about 2 to about 5, preferably from about 3 to about 4.

As used herein, the term "water miscible" means that the organic solvent is soluble in water (i.e., mixes or blends uniformly with water) at least to the degree required to achieve the desired solvent to water ratio in the aqueous composition and preferably the organic solvent is soluble in water in all proportions.

The terms "antimicrobial compound" and "halogenated amide antimicrobial" are used interchangeably herein and refer to halogenated amides which function as biocides (i.e., compounds which inhibit the growth of, or kills, microorganisms such as bacteria, molds, slimes, fungi, etc.).

The term "stabilizing amount" as employed herein refers to an amount of cyclic ether stabilizer sufficient to measurably reduce the decomposition rate of the halogenated amide antimicrobial in the aqueous antimicrobial composition. The aforementioned reduction in the decomposition rate of the halogenated amide antimicrobial is, of course, relative to the decomposition rate encountered with a corresponding aqueous antimicrobial composition in the absence of the cyclic ether stabilizer under the same test conditions. Such reduction is deemed to be "measurable" if it is detectible (and reproducible) by the iodometric test method which is described hereinafter in conjunction with the working examples.

The aqueous antimicrobial compositions of the invention are useful as slimicides in aqueous systems such as paper pulping processes and cooling towers and as sterilizing agents for drycleaning fluids. Such compositions exhibit improved stability toward decomposition of the halogenated amide antimicrobial for extended periods under a wide variety of storage, packaging and handling conditions. They are easily handled and can be employed in the above applications pursuant to conventional techniques such as those described in U.S. Pat. No. 3,689,660.

The indicated process for preparing the aqueous antimicrobial composition is advantageous in that suitably stable compositions can be prepared without separation of the halogenated amide antimicrobial from the aqueous medium in which it was prepared.

DETAILED DESCRIPTION OF THE INVENTION

Halogenated amide antimicrobials employed in the practice of this invention are alpha-haloamides; that is, compounds which contain an amide functionality (i.e., a moiety of the formula —C(O)—N<) and which have at least one halogen atom on a carbon atom located adjacent to (i.e., in the alpha position relative to) the carbonyl group (i.e., the —C(O)— group) of such amide functionality. Advantageously, such halogenated amide antimicrobials are halogenated nitrilopropionamides or halogenated malonic diamides having the formula:

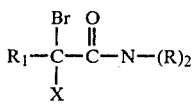

wherein:

X is hydrogen, halogen or a cyano radical, i.e., —C≡N, (preferably hydrogen, chlorine or bromine);

each R group is independently hydrogen, a monovalent "saturated hydrocarbon radical" or an inertly substituted monovalent "saturated hydrocarbon radical" or the two R groups are, jointly, a divalent "saturated hydrocarbon radical", or an inertly substituted divalent "saturated hydrocarbon radical", which, taken with the adjacent nitrogen atom, forms a heterocyclic ring having from 4 to about 10 ring members; and $R_1$ is a cyano radical (i.e., —C≡N) or an amido radical having the formula:

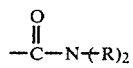

wherein R is as hereinbefore defined. (Preferably $R_1$ is a cyano radical.)

As used herein, the term "saturated hydrocarbon radical" refers to a hydrocarbon radical which is free from aliphatic carbon to carbon unsaturation. Thus, such term includes radicals such as alkyl, cycloalkyl, aryl, alkylaryl, arylalkyl, cycloalkylaryl, etc., and excludes radicals such as alkenyl, cycloalkenyl, alkynyl and the like.

As used herein, the term "inertly substituted saturated hydrocarbon radical" refers to a "saturated hydrocarbon radical" having one or more chain linkages or substituents which are "inert" in the sense that such chain linkages or substituents do not readily react with the ingredients of the aqueous antimicrobial composition. Suitable inertly substituted saturated hydrocarbon radicals thus include, for example, haloalkyl, haloaryl, halocycloalkyl, aminoalkyl, aminoaryl, aminocycloalkyl, hydroxyalkyl, hydroxyaryl, hydroxycycloalkyl, cyanoalkyl, cyanoaryl, cyanocycloalkyl, and the like.

The aforementioned halogenated amide antimicrobials of the formula I thus include brominated nitrilopropionamides (i.e., compounds of the formula I wherein $R_1$ is a cyano radical), such as 2-bromo-3-nitrilopropionamide, 2-bromo-2,3-dinitrilopropionamide, 2,2-dibromo-3-nitrilopropionamide, N-(n-butyl)-2-bromo-3-nitrilopropionamide; N,N-dimethyl-2,2-dibromo-3-nitrilopropionamide, 2-chloro-2-bromo-3-nitrilopropionamide, N-(n-propyl)-2-iodo-2-bromo-3-nitrilopropionamide, N-methyl-N-ethyl-2-fluoro-2-bromo-3-nitrilopropionamide, N-phenyl-2-cyano-2-bromo-3-nitrilopropionamide, N-cyclohexyl-2,2-dibromo-3-nitrilopropionamide, N-benzyl-2-bromo-3-nitrilopropionamide, N-(2,2-dibromo-3-nitrilopropionoyl)-piperidine, and the like.

The aforementioned halogenated amide antimicrobials of the formula I also include mono- and di-bromo malonic diamides (i.e., compounds of the formula I wherein $R_1$ is an amido radical as hereinbefore described), such as 2-bromomalonic diamide, 2,2-dibromomalonic diamide, N-methyl-N'-ethyl-2-chloro-2-bromomalonic diamide, N-phenyl-2-iodo-2-bromomalonic diamide, and the like.

Among the aforementioned halogenated amide antimicrobials, those wherein, in the formula I, $R_1$ is a cyano radical, X is hydrogen, chlorine or bromine and each R is independently hydrogen, lower alkyl (e.g., an alkyl group of from 1 to about 6 carbon atoms) or phenyl are preferred, especially those of the formula I wherein each R independently is hydrogen or methyl and X is hydrogen or bromine. Such halogenated amide antimicrobials include 2-bromo-3-nitrilopropionamide, 2,2-dibromo-3-nitrilopropionamide, N-methyl-2-bromo-3-nitrilopropionamide, N-phenyl-2-bromo-2-chloro-3-nitrilopropionamide, N-methyl-2,2-dibromo-3-nitrilo-propionamide, N,N-dimethyl-2-bromo-3-nitrilopropionamide, N,N-diethyl-2,2-dibromo-3-nitrilopropionamide, and N,N-dimethyl-2,2-dibromo-3-nitrilopropionamide.

Also of particular interest are the dibrominated nitrilopropionamides (i.e., the halogenated amide antimicrobials of the formula I wherein X is bromine and $R_1$ is cyano) wherein each R independently is hydrogen, lower alkyl or phenyl. Such compounds include 2,2-dibromo-3-nitrilopropionamide, N-(n-butyl)-2,2-dibromo-3-nitrilopropionamide, N,N-dimethyl-2,2-dibromo-3-nitrilopropionamide, N-phenyl-N-methyl-2,2-dibromo-3-nitrilopropionamide and the like; especially 2,2-dibromo-3-nitrilopropionamide.

The aqueous antimicrobial compositions of the invention normally contain from about 1 to about 25 percent by weight of the hereinbefore described halogenated amide antimicrobial based upon the total weight of the composition. However, the decomposition of the halogenated amide antimicrobials has been observed to be more pronounced when the aqueous compositions contain less than about 20 percent by weight of the antimicrobial on a total weight basis. Thus, stabilized aqueous antimicrobial compositions which, by virtue of the relatively more pronounced benefits of stabilization, are of particular interest comprise from about 1 to about 15, preferably from about 1 to about 10, most preferably from about 1 to about 5, weight percent of the total composition.

In the composition of this invention, the aforementioned halogenated amide antimicrobial is dissolved in a mixture of water and a water miscible organic solvent. Suitable organic solents include any water miscible organic solvent in which the halogenated amide antimicrobial is at least partially soluble. Preferably the organic solvent is one in which the halogenated amide antimicrobial is soluble at normal room temperature (i.e., from about 20° to about 25° C.) to the extent of at least about 5 parts by weight of the antimicrobial in about 95 parts by weight of the solvent. The most preferred water miscible organic solvents are those in which the antimicrobial is soluble to the extent of at least about 10 (especially at least about 20) parts by weight of the antimicrobial in about 80 parts by weight of the solvent at normal room temperatures (i.e., from about 20° to about 25° C.).

Advantageously, the organic solvent is a polyalkylene glycol or an ether thereof, especially a normally liquid straight chain polyalkylene glycol or a mono- or di-saturated hydrocarbyl ether thereof wherein the term "saturated hydrocarbyl" refers to a monovalent saturated hydrocarbon radical as hereinbefore defined.

Generally, such polyalkylene glycols and polyalkylene glycol ethers have a weight average molecular weight (Mw) of from about 75 to about 1000. Such average molecular weights are hereinafter designated for the particular glycols involved by placing a numeral representing the weight average molecular weight after the glycol name.

Of particular interest in the practice of the invention are the polyalkylene glycols of the ethylene, trimethylene or tetramethylene series and the mono- and di-lower (e.g., containing from 1 to about 6 carbon atoms) saturated hydrocarbyl ethers thereof. Examples of such particularly advantageous solvents include polyethylene glycols, trimethylene glycols, tetramethylene glycols and the mono- and di-lower saturated hydrocarbyl (e.g., lower alkyl and phenyl) ethers of such glycols.

Examples of the aforementioned polyalkylene glycols and ethers include 1,4-butanediol, triethylene glycol, polyethylene glycol 200, tetraethylene glycol, polyethylene glycol 400, diethylene glycol dimethyl ether, diethylene glycol phenyl ether, diethylene glycol ethyl phenyl ether, polytrimethylene glycol 200, diethylene glycol, triethylene glycol methyl ether and polyethylene glycol 600.

Preferably, the polyalkylene glycol or ether ingredient is a polyethylene glycol, or a mixture of polyethylene glycols, having Mw of from about 175 to about 250. Most preferably the polyalkylene glycol ingredient is polyethylene glycol 200.

The amount of the aforementioned water miscible organic solvent employed in the practice of the invention is not particularly critical. Advantageously, however, a sufficient amount is employed to prevent precipitation of the halogenated amide antimicrobial during shipping, storage and use of the aqueous antimicrobial composition. The amount of the organic solvent desirably employed will thus depend upon such factors as the solubility of the halogenated amide antimicrobial in the organic solvent, the desired concentration of the halogenated amide antimicrobial in the composition, and the like. However, as a general rule the organic solvent constitutes from about 5 to about 90, preferably from about 10 to about 80, more preferably from about 25 to about 75, most preferably from about 35 to about 70, percent by weight of the total antimicrobial composition.

As has been noted, any of the aforementioned water miscible organic solvents can be suitably employed in the practice of this invention to dissolve the aforementioned halogenated amide antimicrobial. However, it has been found (and such finding constitutes the subject matter of a commonly owned application by George A. Burk, Charles A. Wilson and Charles E. Reineke filed even date herewith) that the aforementioned problem of halogenated amide decomposition under aqueous conditions is substantially more pronounced in the presence of salts or organic acids and/or glycols having a molecular weight of less than about 70 grams per mole; both of which, for example, are potentially common minor impurities in many commercially available unpurified polyalkylene glycols and ethers thereof. Thus, the benefits attributable to the herein disclosed stabilizers are relatively more pronounced in those stabilized aqueous antimicrobial compositions which employ commercial grades of organic solvents containing the aforementioned impurities or which contain such impurities from some other source.

The amount of water contained by the aqueous antimicrobial composition of the invention is likewise not particularly critical to the practice of the invention. However, as a general rule the compositions of the invention employ water in an amount of from about 5 to about 90, preferably from about 10 to about 85, more preferably from about 15 to about 70, most preferably from about 20 to about 60 weight percent based upon the weight of the total antimicrobial composition.

The cyclic ether stabilizers employed in the practice of this invention are heterocyclic compounds, each having a monocyclic nucleus which is free from carbon-to-carbon unsaturation (i.e., which is saturated) and which contains 5 or 6 ring members. Three of the aforementioned ring members form an ether moiety in the ring structure (i.e., an oxygen atom singly bonded to each of two different carbon atoms) and the remaining 2 or 3 ring members are carbon, oxygen or nitrogen atoms with the proviso that when such remaining ring members comprise 2 oxygen atoms, 2 nitrogen atoms or one oxygen atom and one nitrogen atom, said oxygen and/or nitrogen atoms are separated from each other in the ring structure by a carbon atom. The aforementioned monocyclic nucleus of the cyclic ether stabilizers can be unsubstituted (that is, the available valencies of the ring members, i.e., those valencies which are not employed in forming the ring structure, can be satisfied by hydrogen atoms) or such stabilizers can contain substituents on the ring, such as alkyl groups, aryl groups, arylalkyl groups, alkylaryl groups, etc. which are inert in the sense that they are normally not chemically reactive with all the antimicrobial composition ingredients.

Advantageously, the aforementioned cyclic ether stabilizers correspond to the formula:

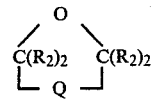

wherein Q represents a 2 or 3 membered divalent organic radical such as $-C(R_2)_2-C(R_2)_2-$, $-C(R_2)_2-O-$, $-C(R_2)_2-C(R_2)_2-C(R_2)_2-$, $-C(R_2)_2-O-C(R_2)_2-$, $-C(R_2)_2-C(R_2)_2-O-$, $-O-C(R_2)_2-O-$, $-C(R_2)_2-N(R_2)-C(R_2)_2-$, etc.; and wherein each $R_2$ is individually hydrogen or a monovalent saturated hydrocarbon radical containing from 1 to about 8 carbon atoms such as lower alkyl (e.g., $C_1$ to about $C_6$ alkyl), phenyl, benzyl, etc.

Examples of such cyclic ether stabilizers include tetrahydrofurans (e.g., tetrahydrofuran, 2-methyltetrahydrofuran, 2-ethyltetrahydrofuran, 2,2-diethyltetrahydrofuran, 2-propyltetrahydrofuran, 3-methyltetrahydrofuran, etc.); tetrahydropyran; 1,3- and 1,4-dioxanes (e.g., 1,3-dioxane, 1,4-dioxane, 4-methyl-1,3-dioxane, 4-methyl-4-phenyl-1,3-dioxane, 2,4-dimethyl-1,3-dioxane, 5-ethyl-4-propyl-1,3-dioxane, 2-phenyl-1,3-dioxane, 4-phenyl-1,3-dioxane, etc.); 1,3-dioxolanes (e.g., 1,3-dioxolane, 2-methyl-1,3-dioxolane, etc.); trioxanes (e.g., 1,3,5-trioxane, 2,4,6-trimethyl-1,3,5-trioxane, 2,4,6-triisopropyl-1,3,5-trioxane, etc.); morpholines (e.g., morpholine, N-methyl morpholine, N-ethyl morpholine, N-butyl morpholine, N-phenyl morpholine, N-benzyl morpholine, etc.); and the like.

Preferred cyclic ether stabilizers for use in the practice of this invention include tetrahydrofuran, 1,4-dioxane, 1,3,5-trioxane and N-methyl morpholine.

The hereinbefore described cyclic ether stabilizer is employed in the practice of the invention in a "stabilizing amount", which term is defined hereinabove. Advantageously, such stabilizer is employed in an amount sufficient to reduce by at least about 20 percent (preferably by at least about 30 percent and most preferably by at least about 40 percent) the amount of antimicrobial compound which decomposes during about 15 days (preferably about 30 days) of storage at 50° C. Such decomposition reduction is, of course, relative to that which occurs under the same conditions in the absence of the aforementioned stabilizer. In quantitative terms, the amount of stabilizer needed to achieve the desired degree of stabilization can vary depending upon the remainder of the composition (i.e., the identity and concentration of the other ingredients in the particular composition involved) and upon the particular stabilizer employed. However, as a general rule the stabilizer constitutes between about 0.05 and about 10, preferably between about 0.1 and about 5, most preferably between about 0.5 and about 2, percent by weight of the total composition.

In addition to the hereinbefore defined ingredients, the aqueous antimicrobial composition of the invention can optionally contain other ingredients. Such optional ingredients can be inert in the sense that they neither inhibit nor accelerate decomposition of the antimicrobial compound. Alternatively, such optional ingredients can themselves be stabilizers for the halogenated amide antimicrobial. Thus, for example, the stabilized aqueous antimicrobial composition of the invention can, in addition to the aforementioned cyclic ether stabilizer, further comprise other compounds which are stabilizers in their own right as disclosed in commonly owned applications filed even date herewith. Such optional additional stabilizers include acide or anhydrides (e.g., acetic acid, ethylenediaminetetraacetic acid, succinic acid, succinic anhydride, glycolic acid, etc.) as disclosed by George A. Burk; carbamoyl or sulfamoyl compounds (e.g., N-methyl urea, N,N-diethyl urea, biuret, sulfamide, oxamide, N,N-dimethylformamide, caprolactam, N-methyl-2-pyrrolidone, dimethylhydantoin, succinimide, etc.) as disclosed by George A. Burk and Charles E. Reineke; aldehydes (e.g., formaldehyde, paraformaldehyde, vanillin, etc.) as disclosed by George A. Burk, Charles A. Wilson and Charles E. Reineke; quaternary salts (e.g., methyl triphenyl phosphonium bromide, n-$C_{12}$-$C_{18}$ alkyl dimethyl benzyl ammonium chloride, etc.) as disclosed by George A. Burk; and azine or nitrile compounds (e.g., cyanuric acid, 2-chloro-4,6-bis(ethylamino)-s-triazine guanidine, succinonitrile, etc.) as disclosed by George A. Burk. The amount of such other stabilizer which is desirably employed varies depending upon a number of factors, such as the identity and amounts of the specific ingredients involved. However, as a general rule between about 0.1 and about 2, preferably between about 0.2 and about 1 percent by weight is employed based upon the total weight of the antimicrobial composition.

The order of combination of the hereinbefore described ingredients is not critical to the obtention of a decreased decomposition rate relative to that obtained with the corresponding non-stabilized composition. However, in order to avoid excessive amounts of decomposition prior to stabilization, it is generally desirable to avoid prolonged exposure of the antimicrobial compound to the water in the composition prior to addition of the stabilizer thereto. Similarly, it is generally desirable, in order to retain optimum antimicrobial activity, to prepare, store, transport and handle the stabilized compositions of the invention at the lowest practicable temperature (normally ambient temperature).

As has been noted, the hereinbefore described stabilizers have been found to reduce the halogenated amide antimicrobial decomposition rate in a mixture of an organic solvent and water. A particularly beneficial result of such phenomenon is that suitably stable halogenated amide antimicrobial compositions can be prepared directly from a mixture of the antimicrobial and the aqueous reaction medium in which it was prepared. Specifically, separation of the halogenated amide antimicrobial from its aqueous reaction medium (which has heretofore been necessary to avoid hydrolytic decomposition) is conveniently eliminated by incorporating such reaction medium into the antimicrobial composition and by counteracting the adverse impact thereof by adding the aforementioned cyclic ether stabilizer.

Thus, in one aspect this invention is a process for preparing the aforementioned stabilized aqueous antimicrobial compositions, which process comprises the steps of (a) preparing the halogenated amide antimicrobial by the acid catalyzed reaction of the corresponding non-halogenated amide wth halogen in aqueous solution; (b) dissolving the resulting aqueous reaction mixture in the hereinbefore described water miscible organic solvent; and (c) adding to the reaction mixture, or to the water soluble organic solvent solution thereof, a stabilizing amount of the aforementioned 5- or 6-membered saturated cyclic ether or an inertly substituted 5- or 6-membered saturated cyclic ether stabilizer. Typically, the aforementioned process also comprises an additional step in which the pH of the reaction mixture, the organic solvent solution, or the stabilized organic solvent soution is adjusted such that the pH of the antimicrobial composition is from about 2 to about 5, preferably from about 3 to about 4. Preferably, such pH adjustment step is performed following preparation of the halogenated amide and prior to dissolution of the reaction mixture in the organic solvent. In such instance adjustment of the pH to a value of from about 5 to about 7 (preferably from about 5.5 to about 6.5) typically provides the antimicrobial composition with a pH within the desired range following the dissolution step.

The particular reagent employed to adjust the pH in the aforementioned step is not particularly critical. However, as a general rule, alkali metal or alkaline earth metal carbonates or bicarbonates (especially sodium carbonate) are advantageously employed.

The preparation of the halogenated amide antimicrobial (i.e., step (a) above) can be accomplished in any convenient conventional manner. Thus, for example, the halogenated amide antimicrobial can be prepared by the acid catalyzed reaction of the corresponding non-halogenated amide (e.g., cyanoacetamide, malonic diamide, and N-substituted derivatives thereof) with halogen (especially bromine) in aqueous solution, preferably at a temperature of less than about 40° C. and preferably at a hydrogen halide (which is a reaction by-product) concentration of less than about 20 weight percent on a total weight basis.

Preferably, however, the initial step of such process is performed pursuant to the improved procedure which is disclosed by U.S. Pat. No. 3,751,444. In such preferred process for preparing the halogenated amide antimicrobial, the improved aspect comprises introducing a water-soluble bromate into the aqueous reaction medium. Further details relating to the practice of such preferred initial step are found in U.S. Pat. No. 3,751,444, the disclosure of which is hereby incorporated by reference.

After the halogenated amide antimicrobial has been prepared in the aforementioned manner, the resulting reaction mixture is dissolved in the hereinbefore described organic solvent. Such dissolution step is performed either before or after addition of the stabilizer and without isolation of the halogenated amide antimicrobial from the aqueous reaction medium. Any of the hereinbefore described water miscible organic solvents can be suitably employed in such dissolution step. However, as has been noted, the presence in such solvent of salts of organic acids and/or glycols having a molecular weight of less than about 70 has been observed to deleteriously affect the stability of the halogenated amide antimicrobial. Accordingly, it is preferable (in order to obtain optimum stability in the resulting compositions of the instant process) to employ an organic solvent of the hereinbefore described type which is substantially free both of salts of organic acids and of glycols having molecular weights of less than about 70 grams per mole.

In the aforementioned process, it is generally desirable to avoid prolonged exposure of the halogenated amide antimicrobial to the aqueous reaction medium in the absence of the stabilizer in order to prevent excessive loss (i.e., decomposition) of the halogenated amide product prior to stabilization. In addition the pH adjustment step is also desirably accomplished without prolonged delay since the decomposition rate of the halogenated amide antimicrobial is generally pH dependent and since such decomposition rate is typically minimized within the indicated pH range. In addition, since the rate of decomposition of the halogenated amide antimicrobial increases with increased temperature, it is preferable to conduct the aforementioned individual process steps (and to store, transport and handle the resulting aqueous antimicrobial compositions) at ambient temperature (e.g., from about 20° to about 25° C. or less in order to avoid excessive decomposition of the antimicrobial during such operations.

Naturally, in the practice of the aforementioned process, other ingredients such as those described hereinbefore, can be added to the aqueous composition either during or after its preparation pursuant to such process.

The practice of the instant invention is further illustrated by the following examples. In such examples all weight percentages are on a total weight basis unless otherwise indicated and the polyethylene glycol 200 employed in such examples is a commercial grade mixture of polyethylene glycols having a weight average molecular weight of about 200 and commercially available as Polyglycol E-200 from The Dow Chemical Company.

Example 1 1,4-Dioxane Stabilization of a Composition Comprising 2,2-dibromo-3-nitrilopropionamide, Polyethylene Glycol 200 and Water These experiments illustrate the increased rate of DBNPA decomposition in the presence of water. The stabilizing effect of 1,4-dioxane upon aqueous 2,2-dibromo-3-nitrilopropionamide (DBNPA) compositions is also illustrated.

EXAMPLE 1

A 2.5 g portion of 2,2-dibromo-3-nitrilopropionamide (DBNPA) is placed in a 2 oz amber bottle. To this is added 23.5 g of polyethylene glycol 200 (P.E.G. 200), 23.5 g of water and 0.5 g of 1,4-dioxane.

Anhydrous Control (i.e., Control 1)

In a second 2 oz amber bottle is placed 2.5 g of DBNPA and 47.5 g of P.E.G. 200.

Aqueous Control (i.e., Control 2)

In a third 2 oz amber bottle is placed 2.5 g of DBNPA, 23.75 g of P.E.G. 200 and 23.75 g of water.

The contents of each of the three bottles are mixed until all of the ingredients are dissolved. The dissolution is accompanied by a temperature rise of about 5° C. After the heat of dissolution has dissipated, the initial DBNPA content is verified by iodometry. The bottles are then closed with a polyethylene lined cap and placed in a constant temperature oven at 50° C. for accelerated decomposition testing. The samples are removed periodically and the extent of DBNPA decomposition is determined by iodometry. The results of the accelerated decomposition testing are presented in Table I below.

In this example (and in the subsequent examples), the relative DBNPA content of the various antimicrobial compositions is determined by iodometry. In such test method, an excess of potassium iodide (KI) is added to the antimicrobial composition and the amount of elemental iodine which has been liberated from the KI (via oxidation of the KI by the DBNPA) is determined by titration with a standard solution of sodium thiosulfate. The amount of DBNPA present in the composition tested is then calculated on the basis of the amount of elemental iodine liberated thereby.

It should be noted that since certain of the intermediate decomposition products of DBNPA are also oxidizing agents, the indicated test method does not, strictly speaking, provide an exact measure of DBNPA content. However, such test method does provide a measure of the amount of DBNPA which has completely decomposed to the ultimate non-oxidizing species and thus provides a relative measure of the stability of the DBNPA compositions tested.

TABLE I

DBNPA CONTENTS AFTER VARIOUS STORAGE PERIODS AT 50° C.

| Example Number | Composition[1] | | | | Initial DBNPA Content | DBNPA Content After the Indicated Storage Period at 50° C.[1] | | |
|---|---|---|---|---|---|---|---|---|
| | P.E.G. 200 | Water | Stabilizer Type | Amount | | 15 Days | 28 Days | 37 Days |
| 1 | 47% | 47% | 1,4-dioxane | 1% | 5.0% | 4.7% | 4.5% | 4.2% |
| Control 1* | 95% | None | None | None | 5.0% | 4.8% | 4.45% | 4.3% |
| Control 2* | 47.5% | 47.5% | None | None | 5.0% | 3.9% | 3.45% | 3.2% |

*Not an example of the invention.
[1]The indicated percentages are in weight percent on a total weight basis.

Comparison of Controls 1 and 2 illustrates the adverse effect of water upon the stability of DBNPA. For example, under aqueous conditions (i.e., Control 2) 36 percent of the DBNPA which was originally present decomposes during 37 days at 50° C., i.e., $[(5.0-3.2) \div 5.0] \times 100\%$. In contrast, the composition of Control 1 (i.e., substantially anhydrous) suffers a loss of only 14 percent of the DBNPA originally percent) over the same time period at 50° C., i.e., $[(5.0-4.3) \div 5.0] \times 100\%$. Similar differences in DBNPA decomposition between Control 2 and Control 1 are reflected at the shorter test intervals.

The stabilizing effect of 1,4-dioxane in the aqueous composition is observed by comparing Example 1 with Control 2. Such comparison shows that the composition of Example 1 exhibits substantially less DBNAP decomposition after each storage interval than does the composition of Control 2 after that same storage interval. In particular, the composition of Example 1 is observed to sustain about 56 percent less DBNPA decomposition than does the composition of Control 2 during 37 days at 50° C., i.e., $[(4.2-3.2) \div (5.0-3.2) \times 100\%$.

Example 2 Aqueous Solution of DBNPA in P.E.G. 200 Stabilized with Trioxane

Example 1 is repeated except that 1,3,5-trioxane (1 weight percent on a total weight basis) is substituted for the 1,4-dioxane of Example 1. After 28 days of storage at 50° C., the trioxane-containing composition of Example 2 exhibits a DBNPA content of 4.4 weight percent on a total weight basis. This represents decomposition of twelve percent (i.e., 0.12) of the initial DBNPA content. In contrast, the corresponding non-stabilized aqueous composition (i.e., Control 2 in Example 1) exhibits decomposition about 31 percent of the initial DBNPA over the same time period at 50° C. Thus, the presence of the trioxane in the composition of Example 2 has prevented about 61 percent, i.e., $[(0.31-0.12)/0.31] \times 100\%$, of the DBNPA decomposition which occurs in its absence over 28 days at 50° C.

Example 3 Aqueous Solution of DBNPA in P.E.G. 200 Stabilized with Tetrahydrofuran The procedure of Example 1 is again repeated except that tetrahydrofuran (1 weight on a total weight basis) is substituted for the 1,4-dioxane in the composition of Example 1. After 28 days of storage at 50° C., the tetrahydrofuran-containing composition of Example 3 exhibits a DBNPA content of 4.55 weight percent, i.e., about 91 percent of the initial 5 weight percent DBNPA content. In contrast, a corresponding non-stabilized aqueous composition (i.e., Control 2 in Example 1) exhibits a retained DBNPA content of only 3.45 weight percent after the same time period at 50° C., i.e., about 69 percent of the initial 5 weight percent DBNPA content.

Thus, the presence of the tetrahydrofuran in the composition of Example 3 has prevented about 71 percent, i.e., $[(4.55-3.45) \div (5.0-3.45)] \times 100\%$, of the DBNPA decomposition which occurs in its absence during 28 days storage at 50° C.

Example 4 Aqueous Solution of DBNPA in P.E.G. 200 Prepared Directly from the Aqueous DBNPA Reaction Medium and Stabilized with N-Methyl Morpholine A 26.0 g quantity (i.e., 0.3 mole) of commercial cyanoacetamide is dissolved in 95 ml of water and is then reacted with a 48 g portion (i.e., 0.3 mole) of bromine for half an hour at 22°-26° C. Thereafter, a 15.1 g portion of $NaBrO_3$ (in the form of a concentrated aqueous solution thereof) is slowly added to the reaction mixture over a 1½ hour period while continuing the reaction at 22°-26° C. An additional 2.0 g portion of bromine is then added and the reaction is continued for an additional 2 hour period.

The pH of the resulting reaction mixture is then adjusted to 6.0 with $Na_2CO_3$ and a 180 gram portion of polyethylene glycol 200 is added to dissolve the reaction mixture. The resultant solution has a pH of 3.5 and contains 19.3 weight percent DBNPA as determined by iodometric titration; representing a 98 percent yield of DBNPA.

One portion of the resulting solution is stabilized with 0.5 weight percent N-methyl morpholine (thereby forming the composition of Example 4) and is analyzed (by iodometric titration) for retained DBNPA content after various storage intervals at 50° C.

A second portion of the resulting reaction mixture solution is stored, without stabilization, at 50° C. and analyzed for retained DBNPA in the same fashion for comparison. The results for both compositions are summarized below.

|  | Stabilizer | DBNPA Content After the Indicated Period at 50° C. | |
| --- | --- | --- | --- |
|  |  | 9 Days | 24 Days |
| Example 4 | 0.5 wt % N-methyl morpholine | 18.5% | 17.2% |
| Non-stabilized Aqueous Control* | None | 17.9% | 14.6% |

*Not an example of the invention.

The foregoing results show that the stabilized aqueous composition of Example 4 exhibits significantly higher DBNPA content than does the corresponding nonstabilized aqueous control after both test intervals. In particular, it is noted that, after 24 days at 50° C., the stabilized composition has suffered 55 percent less DBNPA decomposition (i.e., $[(17.2-14.6) \div (19.3-14.6)] \times 100\%$) than has the corresponding non-stabilized aqueous control.

Pursuant to the procedure of Example 3, t-butyl glycidol ether and 5-hydroxy-2-(chloromethyl)-4-pyrone are each tested as stabilizer candidates in compositions containing 5 weight percent DBNPA, 47 weight percent P.E.G. 200, 47 weight percent water and 1 weight percent of the stabilizer candidate. In such compositions, neither stabilizer candidate provides significant stabilization during storage at 50° C.

While the practice of the invention has been illustrated with reference to particular embodiments and examples, it should be understood that such embodiments and examples are not intended to limit the scope of the instantly claimed invention.

What is claimed is:

1. An aqueous antimicrobial composition having a pH of from about 2 to about 5 and comprising:
    (a) an alpha-halogenated amide antimicrobial compound of the formula:

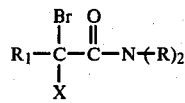

wherein:
X is hydrogen, halogen or a cyano radical;
each R group is independently hydrogen, a monovalent saturated hydrocarbon radical or an inertly substituted monovalent saturated hydrocarbon radical or the two R groups are jointly a divalent saturated hydrocarbon radical or an inertly substituted divalent saturated hydrocarbon radical which, taken with the adjacent nitrogen atom, forms a heterocyclic ring having from 4 to about 10 ring members; and
$R_1$ is a cyano radical or an amido radical of the formula:

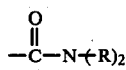

wherein R is as hereinbefore defined;
(b) a water-miscible organic solvent in an amount sufficient to dissolve the halogenated amide antimicrobial, said solvent being a normally liquid polyalkylene glycol of the ethylene, trimethylene or tetramethylene series or a mono- or di-saturated hydrocarbyl ether thereof;
(c) water; and
(d) a stabilizing amount of a 5- or 6-membered saturated cyclic ether or an inertly substituted 5- or 6-membered saturated cyclic ether, said stabilizing amount being an amount sufficient to measurably reduce the decomposition of the halogenated amide antimicrobial in the aqueous composition and said cyclic ether corresponding to the formula:

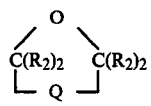

wherein Q represents divalent organic radical of the formula —C($R_2$)$_2$—C($R_2$)$_2$—, —C($R_2$)$_2$—O—, —C($R_2$)$_2$—C($R_2$)$_2$—C($R_2$)$_2$—, —C($R_2$)$_2$—O—C($R_2$)$_2$—, —C($R_2$)$_2$—C($R_2$)$_2$—O—, —O—C($R_2$)$_2$—O—, or —C($R_2$)$_2$—N($R_2$)—C($R_2$)$_2$—and wherein each $R_2$ is individually hydrogen or a monovalent saturated hydrocarbon radical containing from 1 to about 8 carbon atoms.

2. The composition of claim 1 wherein the polyalkylene glycol or ether thereof has a weight average molecular weight of from about 75 to about 1000.

3. The composition of claim 1 wherein, in the antimicrobial compound,
X is hydrogen, bromine or chlorine;
each R group is independently hydrogen, a monovalent saturated hydrocarbon radical or an inertly substituted monovalent saturated hydrocarbon radical; and
$R_1$ is a cyano radical.

4. The composition of claim 1 wherein, in the antimicrobial compound:
X is hydrogen, chlorine or bromine and
$R_1$ is a cyano radical.

5. The composition of claim 1 wherein the antimicrobial compound is 2,2-dibromo-3-nitrilopropionamide.

6. The composition of claim 1 wherein each $R_2$ substituent of the cyclic ether is individually hydrogen, an alkyl group containing from 1 to about 6 carbon atoms, a phenyl radical or a benzyl radical.

7. The composition of claim 1 wherein the cyclic ether is tetrahydrofuran, 1,4-dioxane, 1,3,5-trioxane or N-methyl morpholine.

8. The composition of claim 7 wherein the water-soluble organic solvent is polyethylene glycol, having a weight average molecular weight of about 200; the antimicrobial compound is 2,2-dibromo-3-nitrilopropionamide; and the pH of the aqueous antimicrobial composition is from about 3 to about 4.

9. The composition of claim 1 wherein:
(a) the antimicrobial compound constitutes from about 1 to about 25 weight percent of the total composition;
(b) the water constitutes from about 20 to about 60 weight percent of the total composition;
(c) the water miscible organic solvent constitutes from about 25 to about 75 weight percent of the total composition; and
(d) the cyclic ether constitutes from about 0.1 to about 5 weight percent of the total composition.

10. A process for preparing the aqueous antimicrobial composition of claim 1 which process comprises the steps of:
(a) preparing the alpha-halogenated amide antimicrobial by the acid catalyzed reaction of the corresponding nonhalogenated amide with halogen in aqueous solution, at a temperature of less than about 40° C., and in the presence of hydrogen halide at a concentration which is less than about 20 weight percent on a total weight basis but which is sufficient to catalyze the reaction;
(b) dissolving the resulting aqueous reaction mixture in the water miscible organic solvent;
(c) adding to the reaction mixture of step (a), or to the water miscible organic solvent solution of step (b), a stabilizing amount of the cyclic ether stabilizer; and
(d) adjusting the pH of the product of step (a), (b) or (c) such that the aqueous antimicrobial composition has a pH of from about 2 to about 5.

11. The process of claim 10 in which the pH adjustment is such that the aqueous antimicrobial composition has a pH of from about 3 to about 4.

12. The process of claim 10 wherein the halogenated amide antimicrobial is 2,2-dibromo-3-nitrilopropionamide and the halogen is bromine; the water-miscible organic solvent is polyethylene glycol, or a lower alkyl ether thereof, having a weight average molecular weight of about 200; and the cyclic ether is tetrahydrofuran, 1,4-dioxane, 1,3,5-trioxane or N-methyl morpholine.

13. The process of claim 10 wherein a water-soluble bromate is introduced to the aqueous reaction medium during preparation of the halogenated amide antimicrobial; and the pH of the aqueous reaction mixture is adjusted to a value of from about 5 to about 7 by the addition of an alkali metal, or an alkaline earth metal, carbonate or bicarbonate to such reaction mixture following the preparation of the halogenated amide and prior to the dissolution of such reaction mixture in the organic solvent.

14. An aqueous antimicrobial composition having a pH of from about 2 to about 5 and comprising, based upon the total weight of such composition:

(a) from about 1 to about 25 weight percent of a halogenated amide antimicrobial of the formula:

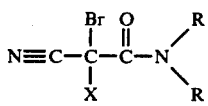

wherein X is hydrogen, chlorine or bromine and each R is independently hydrogen, an alkyl group of from 1 to about 6 carbon atoms or phenyl;
(b) from about 5 to about 90 weight percent of water;
(c) from about 5 to about 90 weight percent of a water-miscible organic solvent which is selected from the group consisting of polyethylene glycols, trimethylene glycols, tetramethylene glycols and the mono- and di- phenyl or $C_1$ to about $C_6$ alkyl ethers thereof and which has a weight average molecular weight of from about 75 to about 1000; and
(d) a stabilizing amount, in the range of from about 0.05 to about 10 weight percent, of a cyclic ether of the formula:

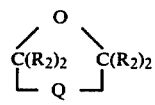

wherein Q represents divalent organic radical of the formula  —C($R_2$)$_2$—C($R_2$)$_2$—,  —C($R_2$)$_2$—O—, —C($R_2$)$_2$—C($R_2$)$_2$—C($R_2$)$_2$—,  —C($R_2$)$_2$—O—C($R_2$)$_2$—,  —C($R_2$)$_2$—C($R_2$)$_2$—O—,  —O—C($R_2$)$_2$—O—, or —C($R_2$)$_2$—N($R_2$)—C($R_2$)$_2$—and wherein each $R_2$ is individually hydrogen, an alkyl group of from 1 to about 6 carbon atoms, phenyl or benzyl.

15. The composition of claim 14 wherein the halogenated amide antimicrobial is 2,2-dibromo-3-nitrilopropionamide.

16. The composition of claim 15 wherein the water-miscible organic solvent is polyethylene glycol having a weight average molecular weight of from about 175 to about 250.

17. The composition of claim 15 wherein the water-miscible organic solvent is polyethylene glycol 200.

18. The composition of claim 16 wherein the cyclic ether is tetrahydrofuran, 1,4-dioxane, 1,3,5-trioxane or N-methyl morpholine.

19. A process for preparing the aqueous antimicrobial composition of claim 18 which process comprises the steps of:
(a) preparing the 2,2-dibromo-3-nitrilopropionamide by the reaction of cyanoacetamide with bromine in aqueous solution (1) at a temperature of less than about 40° C., (2) in the presence of HBr at a concentration which is less than about 20 weight percent on a total weight basis but which is sufficient to catalyze the reaction and (3) in the presence of an alkali metal or an alkaline earth metal bromate;
(b) dissolving the resulting aqueous reaction mixture in the polyethylene glycol having a weight average molecular weight of from about 175 to about 250;
(c) adding to the reaction mixture of step (a) or to the solution thereof of step (b) a stabilizing amount of tetrahydrofuran, 1,4-dioxane, 1,3,5-trioxane or N-methyl morpholine; and
(d) adjusting the pH of the product of step (a), (b) or (c) such that the aqueous antimicrobial composition has a pH of from about 2 to about 5.

* * * * *

UNITED STATES PATENT AND TRADEMARK OFFICE
CERTIFICATE OF CORRECTION

PATENT NO. : 4,190,668
DATED : February 26, 1980
INVENTOR(S) : George A. Burk and Charles A. Wilson It is certified that error appears in the above-identified patent and that said Letters Patent are hereby corrected as shown below:

Col. 1, line 55, delete "ester" and insert --ether--.

Col. 4, line 49, delete "solents" and insert --solvents--.

Col. 5, line 58, delete "or", second occurrence, and insert -- of --.

Col. 7, line 3, delete "hereinabove." and insert --hereinbefore.--.

Col. 7, line 36, delete "acide" and insert --acids--.

Col. 8, line 37, delete "soution" and insert --solution--.

Col. 9, line 41, after "25°C." insert --)--.

Col. 11, line 8, delete "percent)" and insert --present)--.

Col. 11, line 16, delete "DBNAP" and insert --DBNPA--.

Col. 11, line 45, after "weight" (first occurrence) insert --percent--.

Signed and Sealed this

Twenty-fourth Day of June 1980

[SEAL]

Attest:

SIDNEY A. DIAMOND

Attesting Officer

Commissioner of Patents and Trademarks